US005235982A

United States Patent [19]

O'Donnell

[11] Patent Number: 5,235,982

[45] Date of Patent: Aug. 17, 1993

[54] DYNAMIC TRANSMIT FOCUSING OF A STEERED ULTRASONIC BEAM

[75] Inventor: Matthew O'Donnell, Ann Arbor, Mich.

[73] Assignee: General Electric Company, Schenectady, N.Y.

[21] Appl. No.: 767,460

[22] Filed: Sep. 30, 1991

[51] Int. Cl.[5] .................... A61B 8/00

[52] U.S. Cl. .................... 128/660.07; 73/625

[58] Field of Search .................... 128/660.06, 660.07, 128/661.01; 73/625, 626

[56] References Cited

U.S. PATENT DOCUMENTS

| | | | |
|---|---|---|---|
| 4,154,113 | 5/1979 | Engeler | 73/626 |
| 4,155,258 | 5/1979 | Engeler et al. | 73/626 |
| 4,155,259 | 5/1979 | Engeler | 73/626 |
| 4,155,260 | 5/1979 | Engeler et al. | 73/626 |
| 4,180,790 | 12/1979 | Thomas | 367/7 |
| 4,217,684 | 8/1980 | Brisken et al. | 29/25.35 |
| 4,425,525 | 1/1984 | Smith et al. | 310/336 |
| 4,441,503 | 4/1984 | O'Donnell | 128/660 |
| 4,470,303 | 9/1984 | O'Donnell | 73/602 |
| 4,470,305 | 9/1984 | O'Donnell | 73/626 |
| 4,569,231 | 2/1986 | Carnes et al. | 73/626 |
| 4,662,223 | 5/1987 | Riley et al. | 73/626 |
| 4,669,314 | 6/1987 | Magrane | 73/610 |
| 4,809,184 | 2/1989 | O'Donnell et al. | 364/413.25 |
| 4,839,652 | 6/1989 | O'Donnell et al. | 341/122 |
| 4,852,577 | 8/1989 | Smith et al. | 128/660.07 |
| 4,896,287 | 1/1990 | O'Donnell et al. | 364/754 |
| 4,983,970 | 1/1991 | O'Donnell et al. | 341/122 |
| 4,989,143 | 1/1991 | O'Donnell et al. | 128/661.01 X |
| 5,014,712 | 5/1991 | O'Donnell | 128/661.01 |
| 5,113,866 | 5/1992 | Hassler et al. | 128/661.01 |

OTHER PUBLICATIONS

S. C. Leavitt et al., "A Scan Conversion Algorithm for Displaying Ultrasound Images", Hewlett-Packard Journal, Oct. 1983, pp. 30–34.

*Primary Examiner*—Francis Jaworski
*Attorney, Agent, or Firm*—Marvin Snyder

[57] ABSTRACT

A phased array sector scanning (PASS) ultrasonic imaging system produces a fixed focus, steered transmit beam with an array of transducer elements. A receiver forms the echo signals received from an ultrasonic energy reflecting object at the array elements into a receive beam steered in the same direction as the transmit beam and dynamically focused. A midprocessor in the receiver makes corrections to the receive beam samples to offset errors caused by the transmit beam being out of focus at all but its fixed focal range.

8 Claims, 9 Drawing Sheets

DYNAMIC TRANSMIT FOCUSING OF A STEERED ULTRASONIC BEAM

BACKGROUND OF THE INVENTION

This invention relates to coherent imaging using vibratory energy, such as ultrasound and the like and, in particular, to ultrasound imaging using phased array sector scanning.

There are a number of modes in which ultrasound can be used to produce images of objects. The ultrasound transmitter may be placed on one side of the object and the sound transmitted through the object to the ultrasound receiver which is placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode). The present invention relates to a backscatter method for producing ultrasound images.

There are a number of well-known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the reflectors in the object and the time delay is proportional to the range of the reflectors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the reflectors can be reconstructed.

In the so-called C-scan method, the transducer is scanned across a plane above the object and only the echoes reflecting from the focal depth of the transducer are recorded. The sweep of the electron beam of a CRT display is synchronized to the scanning of the transducer so that the x and y coordinates of the transducer correspond to the x and y coordinates of the image.

Ultrasonic transducers for medical applications are constructed from one or more piezoelectric elements sandwiched between a pair of electrodes. Such piezoelectric elements are typically constructed of lead zirconate titanate (PZT), polyvinylidene difluoride (PVDF), or PZT ceramic/polymer composite. The electrodes are connected to a voltage source, and when a voltage is applied, the piezoelectric elements change in size at a frequency corresponding to that of the applied voltage. When a voltage pulse having an ultrasonic frequency is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231, all of which are assigned to the instant assignee.

When used for ultrasound imaging, the transducer typically has a number of piezoelectric elements arranged in an array and driven with separate voltages (apodizing). By controlling the time delays (or phase) and amplitude of the applied voltages, the ultrasonic waves produced by the piezoelectric elements (transmission mode) combine to produce a net ultrasonic wave focused at a selected point. By controlling the time delays and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delays (and/or phase shifts) and gains to the signal from each transducer array element.

This form of ultrasonic imaging is referred to as "phased array sector scanning", or "PASS". Such a scan is comprised of a series of measurements in which the focused ultrasonic wave is transmitted, the system switches to receive mode after a short time interval, and the reflected ultrasonic wave is received and stored. Typically, the transmission and reception are set to the same focal point during each measurement to acquire data from that focal point, and the focal point is changed from measurement to measurement to methodically acquire data from the entire region of interest during the scan. The time required to conduct the entire scan is a function of the time required to make each measurement and the number of measurements required to cover the entire region of interest at the desired resolution and signal-to-noise ratio. A number of such ultrasonic imaging systems are disclosed in U.S. Pat. Nos. 4,155,258; 4,155,260; 4,154,113; 4,155,259; 4,180,790; 4,470,303; 4,662,223; 4,669,314 and 4,809,184, all of which are assigned to the instant assignee.

The ability of present-day ultrasonic imaging systems to dynamically focus the ultrasonic energy while in the receive mode far exceeds the ability to dynamically focus while in the transmit mode. This is because the ultrasonic energy is transmitted in a pulse which travels to all ranges, whereas the time at which the resulting echo signal is received following the launching of the transmitted pulse is a function of the range from which the echo was launched. Consequently, the phase delays produced during the reception of the echo signal can be continuously changed to dynamically focus the receiver at the same range from which the echo signal was reflected.

The inability to dynamically focus the transmit beam results in reduced signal-to-noise ratio and resolution in the reconstructed image. The transmit beam is typically focused at a range ($R_0$) in the center of the field of view.

Image quality is best at this range ($R_0$) and deteriorates as a function of distance from this central range ($R_0$).

SUMMARY OF THE INVENTION

The present invention relates to a method and system for correcting received ultrasonic beams for errors caused by fixed focused ultrasonic transmit beams. More specifically, the present invention includes means for transmitting a steered ultrasonic beam focused at a fixed range, means for receiving an echo signal produced by the steered ultrasonic beam and forming a steered and dynamically focused receive beam $S(R,\theta)$, means for storing samples of steered received beams at successive ranges, means for storing $2N+1$ complex aperture correction coefficients for each of the successive ranges (R); and means for correcting each stored beam sample $S(R,\theta)$ by summing the complex product of each successive aperture correction coefficient for the same range (R) times respective adjacent beam samples $S(R,\theta-N)$ through $S(R,\theta+N)$. The complex aperture correction coefficients are calculated for each transducer array structure and transmit focal distance and are stored in memory for use during the procedure. The corrected beam sample $S'(R,\theta)$ may be supplied to a display where it controls the intensity of an image pixel.

Except at its focal range, the transmit beam is out of focus and insonifies reflectors to each side of the steering angle ($\theta$). For a given transducer array structure and transmit beam focal distance ($R_0$), a set of aperture correction coefficients can be calculated for each range (R) to be sampled. At the focal distance ($R_0$), the aperture correction coefficients are all zero except the central value at the steering angle ($\theta$) which is equal to "1". The magnitude of the central value declines with distance from the focal range ($R_0$) and the magnitudes of adjacent values increase to reflect the fact that the transmit beam "spreads" laterally to each side of the steering angle ($\theta$). While the calculation of these aperture correction coefficients is an onerous task, they can be performed off-line and stored for later use during the imaging procedure.

Accordingly, one object of the invention is to correct ultrasonic receive beam data to account for the fact that the ultrasonic transmit beam has a fixed focal point.

In the preferred embodiment, data corrections can be made on an entire receive beam at the angle ($\theta$) when data for it and the four closest beams have been acquired. The calculations for making these corrections are such that data are produced for the system display on a real-time basis without significantly slowing the production of an image.

Accordingly, another object of the invention is to perform the data corrections on receive beam data in real time.

The features of the invention believed to be novel are set forth with particularity in the appended claims. The invention itself, however, both as to organization and method of operation, together with further objects and advantages thereof, may best be understood by reference to the following description taken in conjunction with the accompanying drawing(s) in which:

BRIEF DESCRIPTION OF THE DRAWINGS

FIGS. 5a–5e are graphical illustrations of the signal at various points in the receiver channel of FIG. 5;

DESCRIPTION OF THE PREFERRED EMBODIMENT

Figure 1:
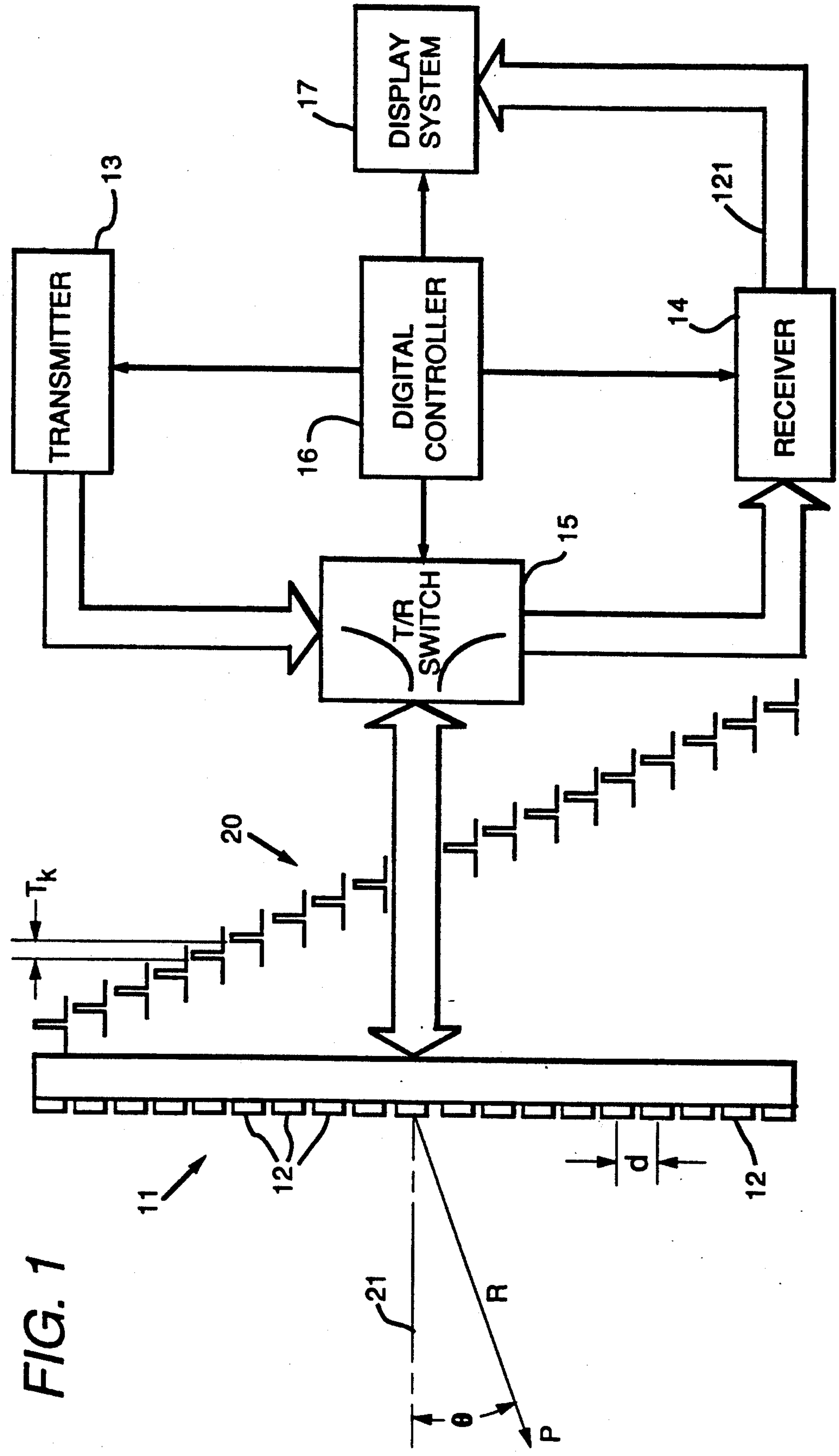
FIG. 1 is a block diagram of an ultrasonic imaging system which employs the present invention.

Referring particularly to FIG. 1, an ultrasonic imaging system includes a transducer array 11 comprised of a plurality of separately driven elements 12 which each produce a burst of ultrasonic energy when energized by a pulse produced by a transmitter 13. The ultrasonic energy reflected back to transducer array 11 from the subject under study is converted to an electrical signal by each transducer element 12 and applied separately to a receiver 14 through a set of switches 15. Transmitter 13, receiver 14 and switches 15 are operated under control of a digital controller 16 responsive to the commands input by a human operator. A complete scan is performed by acquiring a series of echoes in which transmitter 13 is gated on momentarily to energize each transducer element 12, switches 15 are then gated on to receive the subsequent echo signals produced by each transducer element 12, and these separate echo signals are combined in receiver 14 to produce a single echo signal which is employed to produce a pixel or a line in an image on a display 17.

Transmitter 13 drives transducer array 11 such that the ultrasonic energy produced is directed, or steered, in a beam. A B-scan can therefore be performed by moving this beam through a set of angles from point-to-point rather than physically moving transducer array 11. To accomplish this, transmitter 13 imparts a time delay ($T_k$) to the respective pulses 20 that are applied to successive transducer elements 12. If the time delay is zero ($T_k=0$), all the transducer elements 12 are energized simultaneously and the resulting ultrasonic beam is directed along a central axis 21 normal to the transducer face and originating from the center of transducer array 11. The beam is focused at an infinite range. As the time delay ($T_k$) is increased, as illustrated in FIG. 1, the ultrasonic beam is directed downward from central axis 21 by an amount $\theta$. The relationship between the time delay increment $T_k$ which is added successively to each $k^{th}$ signal from one end of the transducer array ($k=1$) to the other end ($k=N$) is given by the following relationship:

$$T_k = -(k-(N-1)/2)d\sin\theta/c + (k-(N-1)/2)^2 d^2 \cos^2\theta/2R_0c + T_0 \quad (1)$$

where d=equal spacing between centers of adjacent transducer elements 12;

c=the velocity of sound in the object under study;

$R_0$=range at which transmit beam is focused;

$T_0$=delay offset which insures that all calculated values ($T_k$) are positive values.

The first term in this expression steers the beam in the desired angle $\theta$, and the second is employed when the transmitted beam is to be focused at a fixed range $R_0$. A sector scan is performed by progressively changing the time delays $T_k$ in successive excitations. The angle $\theta$ is thus changed in increments to steer the transmitted beam in a succession of directions, but the focal distance $R_0$ remains fixed. When the direction of the beam is above central axis 21, the timing of pulses 20 is reversed, but the formula of equation (1) still applies.

Figure 6A:
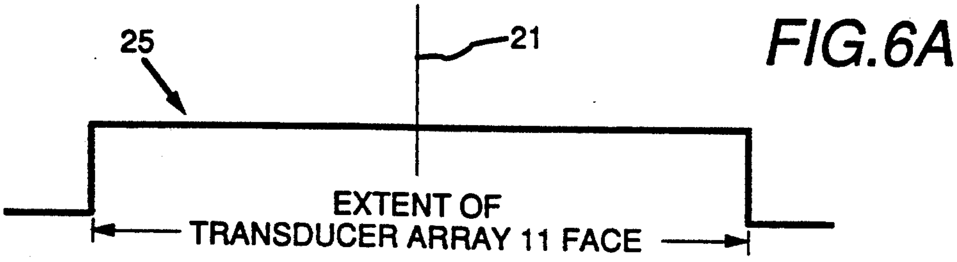
FIGS. 6A–6E are graphical representations of the amplitude and phase of signals across the face of the transducer which forms part of the system of FIG. 1.
Figure 6B:
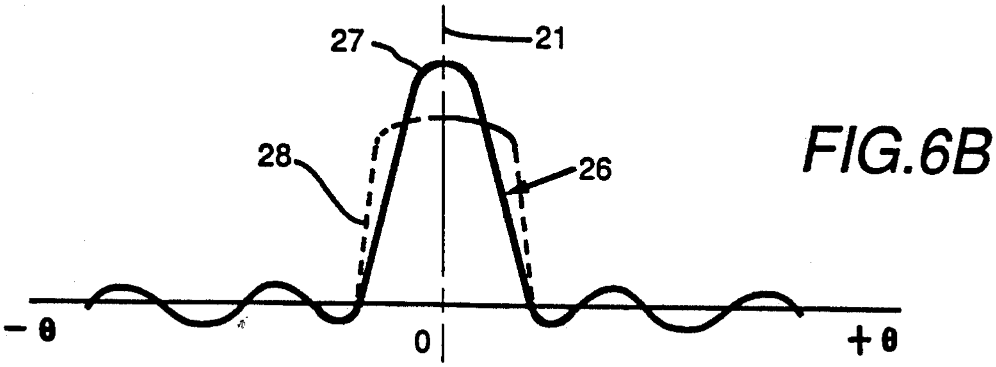

This transmit aperture function is illustrated graphically in FIG. 6A where a solid line 25 indicates that an equal amplitude signal is applied to each element across the face of transducer array 11 of FIG. 1. This constant amplitude aperture function produces the well-known SINC beam pattern 26, illustrated in FIG. 6B. With no time delays ($T_k=0$), this transmit beam is directed along central axis 21 and is focused at infinity. Reflectors located at distant ranges (R) along central axis 21 will be strongly insonified, as indicated by central peak 27 in the SINC beam pattern, while reflectors located to either side will receive only minor insonification by coherent ultrasonic energy. In contrast, at short ranges this transmit beam is "out of focus" and the beam pattern indicated by dashed line 28 results. In this case, the reflectors located on central axis 21 receive less coherent insonification and reflectors located to each side are significantly insonified. The farther the reflectors are from the transmit focal range, the more the coherent insonification spreads laterally to each side of central axis 21.

Figure 6C:
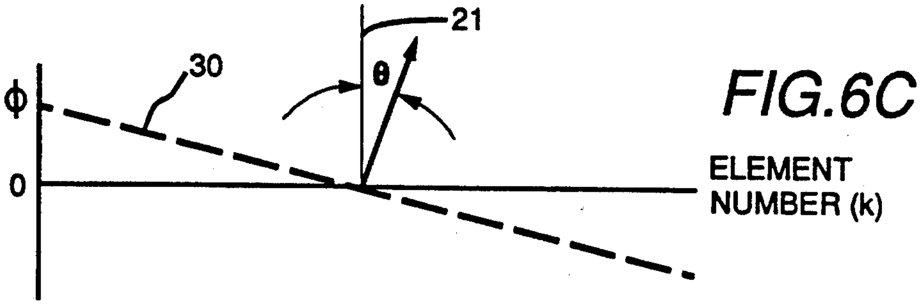
Figure 6D:
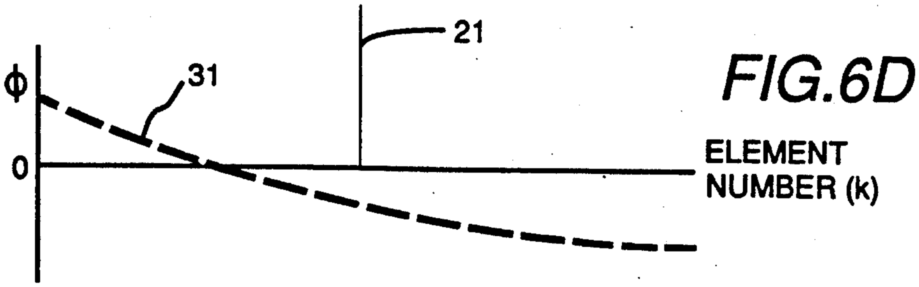

In the above example illustrated in FIG. 6A, the transmit beam is neither steered nor focused by applying the time delays of equation (1). If the steering time delay $T_k$ is employed, the phase ($\phi$) of the ultrasonic energy launched from transducer array 11 changes linearly as a function of transducer array element number (k). This is illustrated in FIG. 6C by dashed line 30 which has a slope that determines the direction of the steered transmit beam. The shape of SINC beam pattern 26 is the same, but the central peak 27 is now steered at an angle $\theta$ off the central axis 21. If a focusing component is added to the delays $T_k$ as provided by the second term in equation (1), the phase ($\phi$) across the face of transducer array 11 changes in a non-linear manner as indicated by the phase aperture function 31 in FIG. 6D. The closer the focal range ($R_0$) is to the surface of transducer array 11, the more curved this phase aperture function becomes.

Figure 6E:
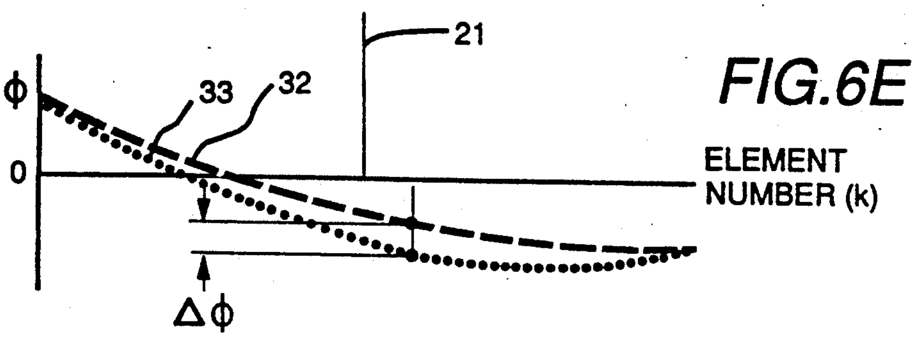

Referring particularly to FIG. 6E, if a transmit beam is produced for a given steering angle ($\theta$) and focal range ($R_0$), the phase aperture function across the face of transducer array 11 is illustrated by the dashed line 32. However, reflectors located at another range (R) would require a phase aperture function as illustrated by dotted line 33 in order to be in focus. In other words, the phase ($\phi$) of each element (k) across the face of transducer 11 must be corrected by an amount $\Delta\phi$ which is the difference in phase between the two aperture functions 32 and 33. This phase correction is given by the following formula:

$$\Delta\phi(k) = [2\pi/\lambda]\,(k-(N-1)/2)^2 d^2 \cos^2\theta \left[\frac{1}{2R} - \frac{1}{2R_0}\right] \quad (2)$$

where k=transducer element number;

$\theta$=steering angle;

R=range of reflectors;

$R_0$=focal range of transmit beam;

$\lambda$=wavelength of ultrasonic energy;

d 32 equal spacing between transducer elements.

In accordance with the present invention, these phase corrections can be transformed into beam pattern space and employed to derive stored aperture correction coefficients to correct each received echo signal to account for the out-of-focus transmit beam. Referring again to FIG. 6B, these corrections in effect correct the out-of-focus beam pattern, indicated by dashed line 28, so that it is in focus as indicated by line 26. As explained in more detail below, this correction involves adding some of the receive signal located on each side of the steering angle ($\theta$) to the signal at the steering angle ( ).

Referring still to FIG. 1, the echo signals produced by each burst of ultrasonic energy emanate from reflecting objects located at successive positions (R) along the ultrasonic beam. These are sensed separately by each segment 12 of transducer array 11 and a sample of the magnitude of the echo signal at a particular time represents the amount of reflection occurring at a specific range (R). Due to differences in the propagation paths between the focal point P and each transducer element 12, however, these echo signals will not occur simultaneously and their amplitudes will not be equal. The function of the receiver 14 is to amplify and demodulate these separate echo signals, impart the proper time delay to each and sum them together to provide a single echo signal which accurately indicates the total ultrasonic energy reflected from focal point P located at range R along the ultrasonic beam oriented at the angle $\theta$.

To simultaneously sum the electrical signals produced by the echoes from each transducer element 12, time delays are introduced into each separate transducer element channel of receiver 14. In the case of linear array 11, the delay introduced in each channel may be divided into two components, one component being a beam steering time delay, and the other component being a beam focusing time delay. The beam steering and beam focusing time delays for reception are precisely the same delays ($T_k$) as the transmission delays described above. However, the focusing time delay component introduced into each receiver channel is continuously changing during reception of the echo to provide dynamic focusing of the received beam at the range R from which the echo signal emanates. This dynamic focusing delay component is as follows:

$$T_k=(k-(N-1)/2)^2 d^2 \cos^2\theta/2Rc \quad (3)$$

R=the range of the focal point P from the center of the array 11;

c=the velocity of sound in the object under study; and $T_k$=the time delay associated with the echo signal from the $k^{th}$ element to coherently sum it with the other echo signals.

Under direction of digital controller 16, receiver 14 provides delays during the scan such that steering of receiver 14 tracks with the direction of the beam steered by transmitter 13 and it samples the echo signals at a succession of ranges and provides the proper delays to dynamically focus at points P along the sampled beam. Thus, each emission of an ultrasonic pulse results in the acquisition of a series of echo signal samples which represent the amount of reflected sound from a corresponding series of points P located along the ultrasonic receive beam.

Display system 17 receives the series of data points produced by receiver 14 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles ($\theta$) is performed to provide the data necessary for display.

Figures 2, 2A, 2B:
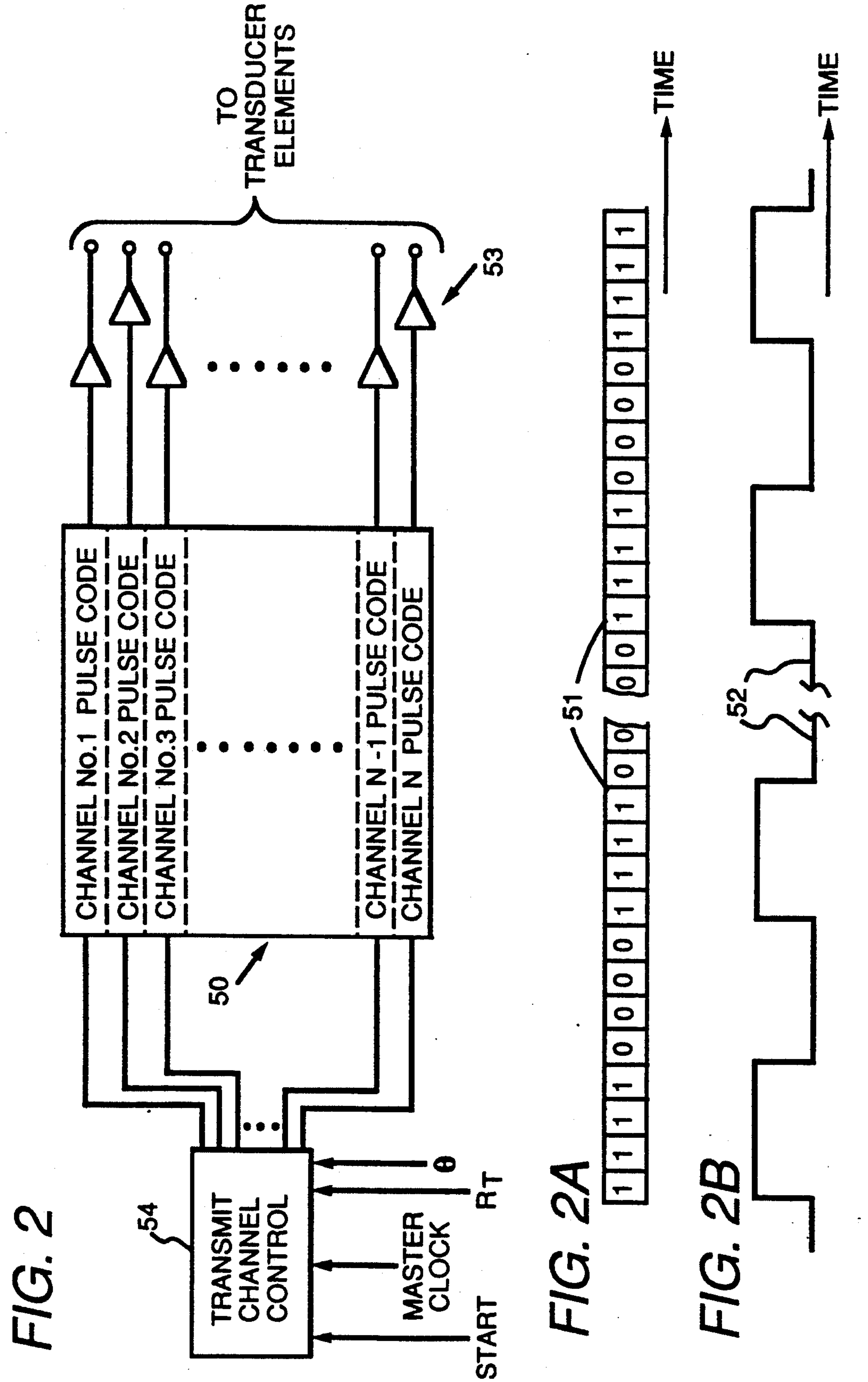
FIG. 2 is a block diagram of a receiver which forms part of the system of FIG. 1.
FIGS. 2A and 2B are graphical illustrations of the signal in any of the channels of transmitter 50 of FIG. 2.

Referring to FIG. 2 in conjunction with FIG. 1, transmitter 13 includes a set of channel pulse code memories indicated collectively at 50. In the preferred embodiment there are 128 separate transducer elements 12, and therefore, there are 128 separate channel pulse code memories 50. Each pulse code memory 50 is typically a 1-bit by 512-bit memory which stores a bit pattern 51 that determines the frequency of ultrasonic pulse 52 that is to be produced. In the preferred embodiment, this bit pattern is read out of each pulse code memory 50 by a 40 MHz master clock and applied to a driver 53 which amplifies the signal to a power level suitable for driving transducer 11. In the example shown in FIG. 2A, the bit pattern is a sequence of four "1" bits alternated with four "0" bits to produce a 5 MHz ultrasonic pulse 52. Transducer elements 12 to which these ultrasonic pulses 52 are applied respond by producing ultrasonic energy. If all 512 bits are used, a pulse of bandwidth as narrow as 40 kHz centered on the carrier frequency (i.e. 5 MHz in the example) will be emitted.

As indicated above, to steer the transmitted beam of ultrasonic energy in the desired direction ($\theta$), pulses 52 for each of the N channels, such as shown in FIG. 2B, must be delayed by the proper amount. These delays are provided by a transmit control 54 which receives four control signals (START, MASTER CLOCK, $R_0$ and $\theta$) from digital controller 16 (FIG. 1). Using the input control signal $\theta$, the fixed transmit focus $R_0$, and the above equation (1), transmit control 54 calculates the delay increment $T_k$ required between successive transmit channels. When the START control signal is received, transmit control 54 gates one of four possible phases of a 40 MHz MASTER CLOCK signal through to the first transmit channel 50. At each successive delay time interval ($T_k$) thereafter, one of four phases of the 40 MHz MASTER CLOCK signal is gated through to the next channel pulse code memory 50 until all n=128 channels are producing their ultrasonic pulses 52. Each transmit channel 50 is reset after its entire bit pattern 51 has been transmitted and transmitter 13 then waits for the next $\theta$ and next START control signals from digital controller 16. As indicated above, in the preferred embodiment of the invention a complete B-scan is comprised of 128 ultrasonic pulses steered in $\Delta\theta$ increments of 0.70° through a 90° sector centered about the central axis 21 (FIG. 1) of the transducer 11.

For a detailed description of transmitter 13, reference is made to commonly assigned U.S. Pat. No. 5,014,712, issued May 14, 1991, and entitled "Coded Excitation For Transmission Dynamic Focusing of Vibratory Energy Beam", incorporated herein by reference.

Figure 3:
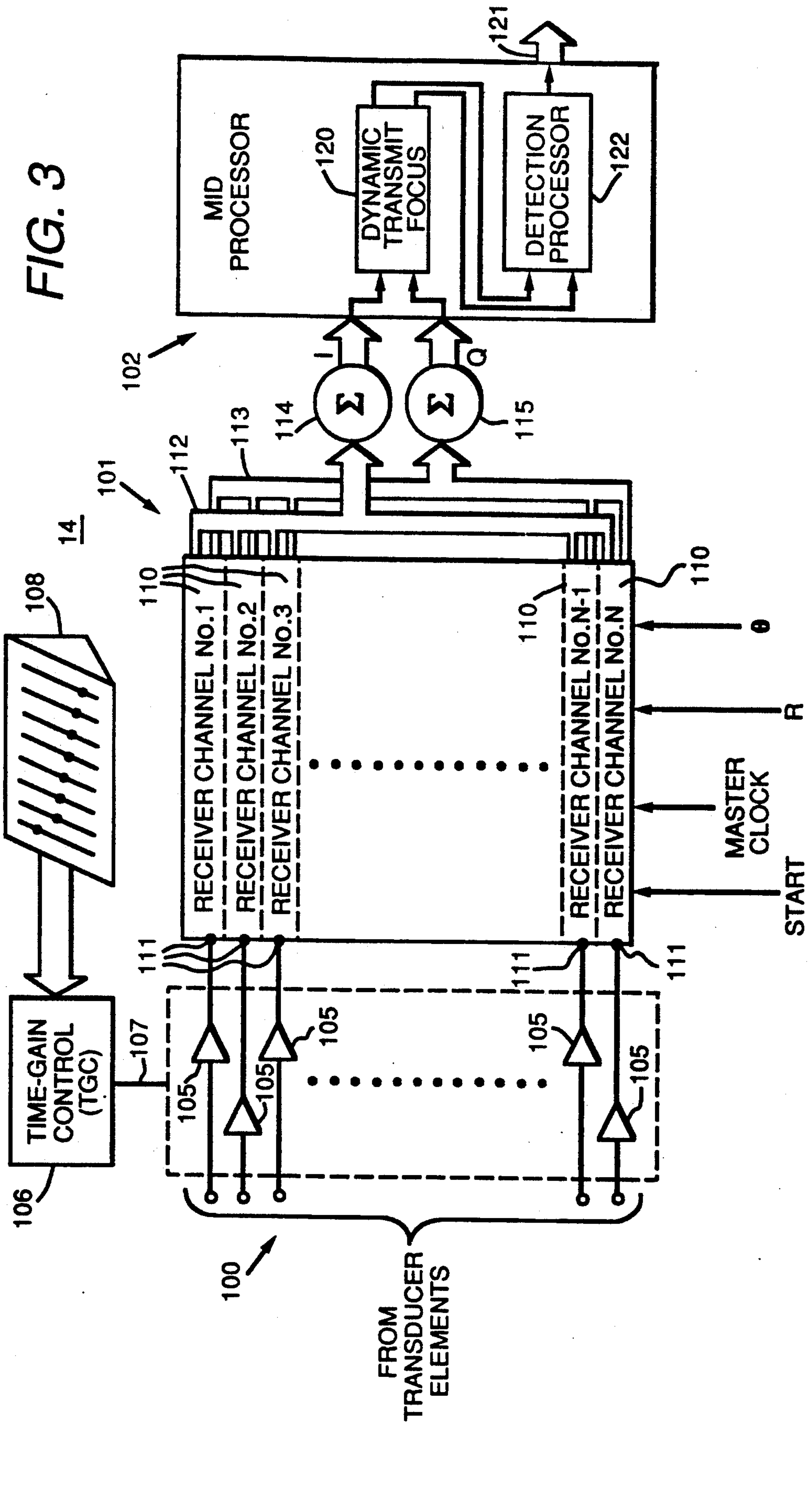
FIG. 3 is a block diagram of a receiver which forms part of the system of FIG. 1.

Referring particularly to FIG. 3 in conjunction with FIG. 1, receiver 14 is comprised of three sections: a time-gain control (TGC) section 100, a receive beam forming section 101, and a mid-processor 102. The time-gain control section 100 includes an amplifier 105 for each of the N=128 receiver channels and a time-gain control circuit 106. The input of each amplifier 105 is connected to a respective one of transducer elements 12 to receive and amplify the echo signal which it receives. The amount of amplification provided by amplifiers 105 is controlled through a control line 107 that is driven by the time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets eight (typically) TGC linear potentiometers 108 to values which provide a relatively uniform brightness over the entire range of the sector scan. The time interval over which the echo signal is acquired determines the range from which it emanates, and this time interval is divided into eight segments by TGC control circuit 106. The settings of the eight potentiometers are employed to set the gain of amplifiers 105 during each of the eight respective time intervals so that the echo signal is amplified in ever increasing amounts over the echo signal acquisition time interval.

The receive beam forming section 101 of the receiver 14 includes N=128 separate receiver channels 110. As will be explained in more detail below, each receiver channel 110 receives the analog echo signal from one of TGC amplifiers 105 at an input 111, and it produces a stream of digitized output values on an I bus 112 and a Q bus 113. Each of these I and Q values represents a sample of the echo signal envelope at a specific range (R). These samples have been delayed in the manner described above such that when they are summed at summing points 114 and 115 with the I and Q samples from each of the other receiver channels 110, they indicate the magnitude and phase of the echo signal reflected from point P located at range R on the steered beam ($\theta$). In the preferred embodiment, each echo signal is sampled at equal intervals of about 150 micrometers over the entire range of the scan line (typically 40 to 200 millimeters).

For a more detailed description of receiver 14, reference is made to U.S. Pat. No. 4,983,970 which issued on Jan. 8, 1991 as is entitled "Method And Apparatus for Digital Phase Array Imaging", and which is incorporated herein by reference.

Referring still to FIG. 3, the mid-processor section 102 receives the beam samples S(R,$\theta$) from summing points 114 and 115. The I and Q values of each beam sample are 16-bit digital numbers representing the in-phase and quadrature components of the magnitude of reflected sound from a sample point S(R,$\theta$). Mid processor 102 can perform a variety of calculations on these beam samples, where choice is determined by the type of image to be reconstructed. In the preferred embodiment the beam samples S(R,$\theta$) are applied to a dynamic transmit focus processor 120 which makes the corrections according to the present invention as will be described in detail below. The in-phase and quadrature components of the corrected samples S'(R,θ) are then applied to a detection processor 122 which calculates a digital magnitude M(R,θ) from each corrected beam sample and produces it at output 121:

$$M(R,\theta) = \sqrt{I^2 + Q^2} \quad (4)$$

where I and Q are the components of corrected sample points S'(R,θ). Receiver 14 thus produces a stream of 8-bit digital numbers M(R,θ) at its output 121 for each beam in the scan.

Figure 4:
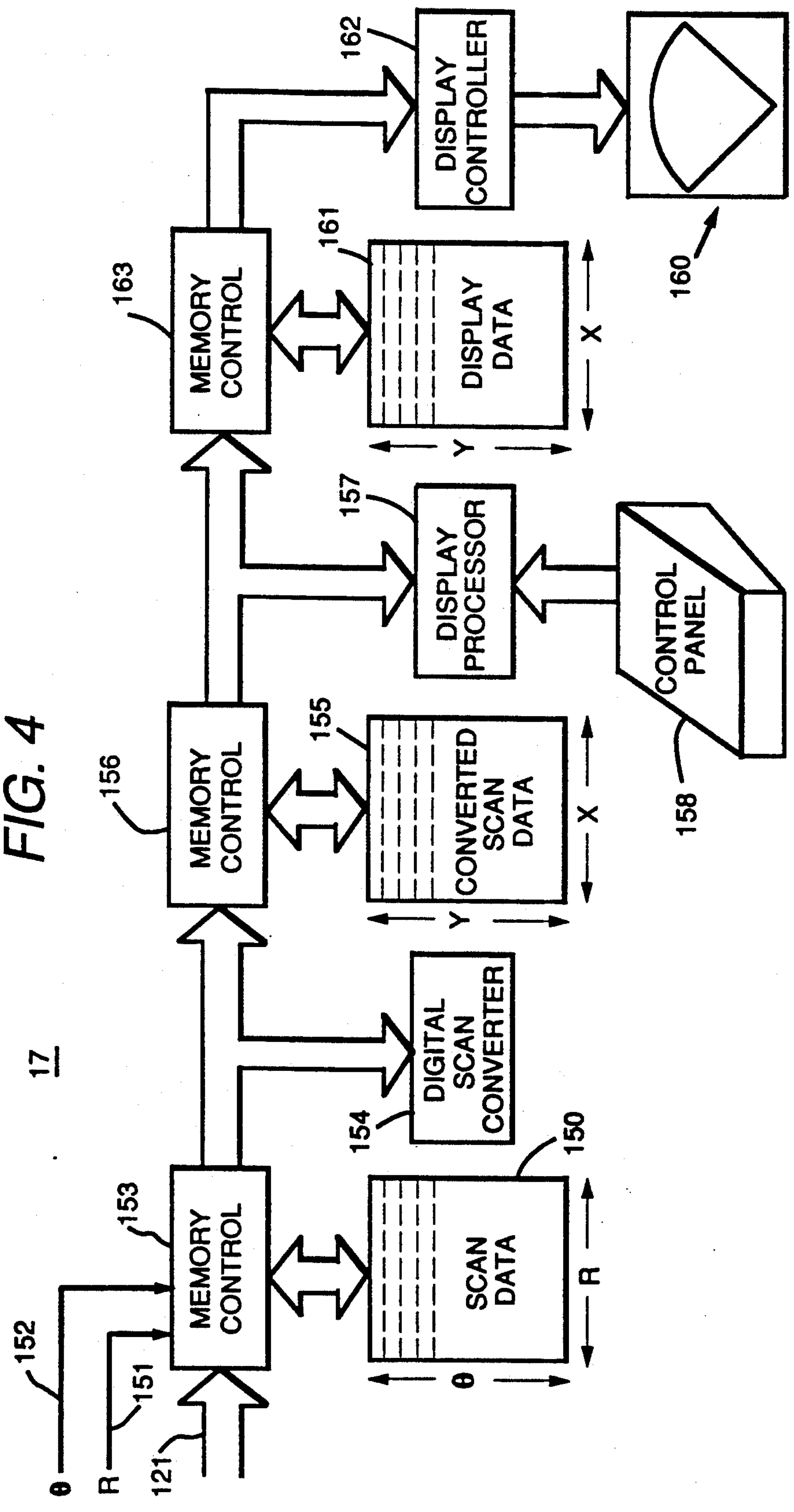
FIG. 4 is a block diagram of a display system which forms part of the system of FIG. 1.

Referring particularly to FIGS. 1 and 4, the output signal of receiver 14 is supplied to the input of the display system 17. This "scan data" is stored in a memory 150 as an array, with the rows of the scan data array 150 corresponding with the respective beam angles (θ) that are acquired, and the columns of the scan data array 150 corresponding with the respective ranges (R) at which samples are acquired along each beam. The R and θ control signals 151 and 152 from receiver 14 indicate where each input value is to be stored in array 150, and a memory control circuit 153 writes that value to the proper memory location in array 150. The scan can be continuously repeated and the flow of values from receiver 14 will continuously update scan data array 150.

Referring still to FIG. 4, the scan data in the array 150 are read by a digital scan converter 154 and converted to a form producing the desired image. If a conventional B-scan image is being produced, for example, the magnitude values M(R,θ) stored in scan data array 150 are converted to magnitude values M(x,y) which indicate magnitudes at pixel locations (x,y) in the image. Such a polar coordinate to Cartesian coordinate conversion of the ultrasonic image data is described, for example, in an article by Steven C. Leavitt et al in *Hewlett-Packard Journal*, Oct., 1983, pp. 30–33, entitled "A Scan Conversion Algorithm for Displaying Ultrasound Images".

Regardless of the particular conversion made by digital scan converter 154, the resulting image data is written to a memory 155 which stores a two-dimensional array of converted scan data. A memory control 156 provides dual-port access to memory 155 such that digital scan converter 154 can continuously update the values therein with fresh data while a display processor 157 reads the updated data. Display processor 157 is responsive to operator commands received from a control panel 158 to perform conventional image processing functions on the converted scan data memory 155. For example, the range of brightness levels indicated by the converted scan data in memory 155 may far exceed the brightness range of display device 160. Indeed, the brightness resolution of the converted scan data in memory 155 may far exceed the brightness resolution of the human eye, and manually operable controls are typically provided which enable the operator to select a window of brightness values over which maximum image contrast is to be achieved. The display processor reads the converted scan data from memory 155, provides the desired image enhancement, and writes the enhanced brightness values to a display memory 161.

Display memory 161 is shared with a display controller circuit 162 through a memory control circuit 163, and the brightness values therein are mapped to control the brightness of the corresponding pixels in display 160. Display controller 162 is a commercially available integrated circuit which is designed to operate the particular type of display 160 which is used. For example, display 160 may be a CRT, in which case display controller 162 is a CRT controller chip which provides the required sync pulses for the horizontal and vertical sweep circuits and maps the display data to the CRT at the appropriate time during the sweep.

It should be apparent to those skilled in the art that the display system 17 may take one of many forms depending on the capability and flexibility of the particular ultrasound system. In the preferred embodiment described above, programmed microprocessors are employed to implement the digital scan converter and display processor functions, and the resulting display system is, therefore, very flexible and powerful.

Figure 5:
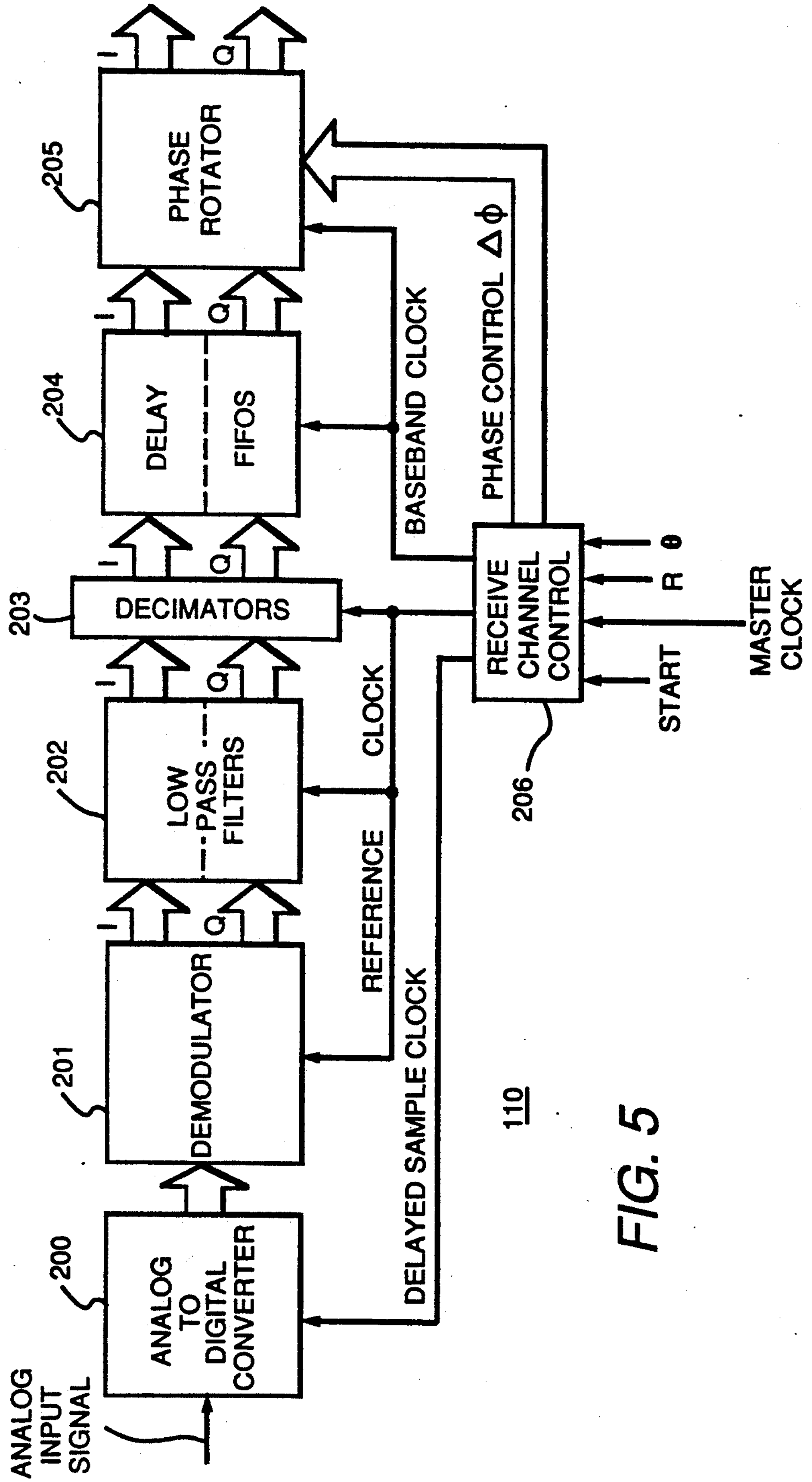
FIG. 5 is a block diagram of a receiver channel which forms part of the receiver of FIG. 3.

As indicated above with reference to FIG. 3, the beam forming section 101 of the receiver 14 is comprised of a set of receiver channels 110—one for each element 12 of transducer 11 (FIG. 1). Referring particularly to FIG. 5, each receiver channel is responsive to a START command, a 40 MHz master clock, a range signal (R) and a beam angle signal (θ) from digital controller 16 (FIG. 1) to perform the digital beam forming functions. These include: sampling the analog input signal in an analog-to-digital converter 200, demodulating the sampled signal in a demodulator 201; filtering out the high frequency sum signals produced by demodulator 201 with low pass filters 202; reducing the data rate in decimators 203; and time delaying and phase adjusting the resulting digital data stream in delay FIFOs 204 and phase rotator 205. All of these elements are controlled by a receive channel control 206 which produces the required clock and control signals in response to commands from digital controller 16 (FIG. 1). In the preferred embodiment, all of these elements are contained on a single integrated circuit.

Referring still to FIG. 5, analog-to-digital converter 200 samples the analog signal, indicated graphically by waveform 210 in FIG. 5A, at regular intervals determined by the leading edge of a delayed sample clock signal from receive channel control 206. In the preferred embodiment the sample clock signal is a 40 MHz clock to enable use of ultrasonic frequencies up to 20 MHz without violating the Nyquist sampling criteria. When a 5 MHz ultrasonic carrier frequency is employed, for example, it is sampled eight times per carrier cycle and a 10-bit digital sample is produced at the output of the analog-to-digital converter at a 40 MHz rate. These samples are supplied to demodulator 201 which mixes each sample with both a reference in-phase with the transmitted ultrasonic carrier, and with a reference in quadrature with the transmitted ultrasonic carrier. The demodulator reference signals are produced from stored SINE and COSINE tables that are read out of their respective ROM memories by a 40 MHz reference clock signal from receive channel control signal 206. The SINE value is digitally multiplied by the sampled input signal to produce a demodulated, in-phase value (I) supplied to low pass filter 202, and the COSINE value is digitally multiplied by the same sampled input signal to produce a demodulated, quadrature phase value Q signal supplied to a separate low pass filter 202. The low pass filters 202 are finite impulse response filters tuned to pass the difference frequencies supplied by demodulator 201, but block the higher, sum frequencies. As shown by waveform 250 in the graph of FIG. 5B, the output signal of each low pass filter is, therefore, a 40 MHZ stream of digital values which indicate the magnitude of the I or Q component of the echo signal envelope.

For a detailed description of an analog-to-digital converter, demodulator, and a low pass filter circuit reference is made to U S. Pat. No. 4,839,652 which issued Jun., 13, 1989 and is entitled "Method and Apparatus For High Speed Digital Phased Array Coherent Imaging System".

Referring still to FIG. 5, the rate at which the demodulated I and Q components of the echo signal is sampled is reduced by decimators 203. The 12-bit digital samples are supplied to the decimators at a 40 MHz rate which is unnecessarily high from an accuracy standpoint, and which is a difficult data rate to maintain throughout the system. Accordingly, decimators 203 select every eighth digital sample to reduce the data rate down to a 5 MHz rate. This corresponds to the frequency of a baseband clock signal produced on receive channel control 206 and employed to operate the remaining elements in the receiver channel. The I and Q output signals of decimators 203 are thus digitized samples 219 of the echo signal envelope indicated by dashed line 220 in the graph of FIG. 5C. The decimation ratio and the baseband clock frequency can be changed to values other than 8:1 and 5 MHz.

The echo signal envelope represented by the demodulated and decimated digital samples is then delayed by delay FIFOs 204 and phase rotator 205 to provide the desired beam steering and beam focusing. These delays are in addition to the coarse delays provided by the timing of the delayed sample clock signal which is applied to analog-to-digital converter 200 as described above. That is, the total delay provided by receiver channel 110 is the sum of the delays provided by the delayed sample clock signal supplied to analog-to-digital converter 200, the delay FIFOs and the phase rotator 205. The delay FIFOs 204 are memory devices into which the successive digital sample values are written as they are produced by decimators 203 at a rate of 5 MHz. These stored values are written into successive memory addresses and then read from the memory device and supplied to phase rotator 205. The amount of the delay, illustrated graphically in FIG. 5D, is determined by the difference between the memory location from which the digital sample is currently being supplied and the memory location into which the currently received digital sample is being stored. The 5 MHz baseband clock signal establishes 200 nanosecond intervals between stored digital samples and the FIFOs 204 can, therefore, provide a time delay measured in 200 nanosecond increments up to their maximum of 25.6 microseconds.

Phase rotators 205 enable the digitized representation of the echo signal to be delayed by amounts less than the 200 nanosecond resolution of delay FIFOs 204. The I and Q digital samples supplied to phase rotator 205 may be represented, as shown in FIG. 5E, by a phasor 221 and the rotated I and Q digital samples produced by phase rotator 205 may be represented by a phasor 222. The magnitudes of the phasors (i.e. the vector sum of the I and Q components of each) are not changed, but the I and Q values are changed with respect to one another such that the output phasor 222 is rotated by an amount $\Delta\phi$ from the input phasor 221. The phase can be either advanced ($+\Delta\phi$) or delayed ($-\Delta\phi$) in response to a phase control signal received on a bus from receive channel control 206. For a detailed description of phase rotator 205, reference is made to commonly assigned U.S. Pat. No. 4,896,287 which issued on Jan. 23, 1990 and is entitled "Cordic Complex Multiplier", incorporated herein by reference.

For a general description of the receiver channel 110 and a detailed description of how the I and Q output signals of each receiver channel 110 are summed together to form a receive beam signal, reference is also made to commonly assigned U.S. Pat. No 4,983,970 which issued on Jan. 8, 1991 and is entitled "Method and Apparatus For Digital Phased Array Imaging", and is incorporated herein by reference.

Figure 7:
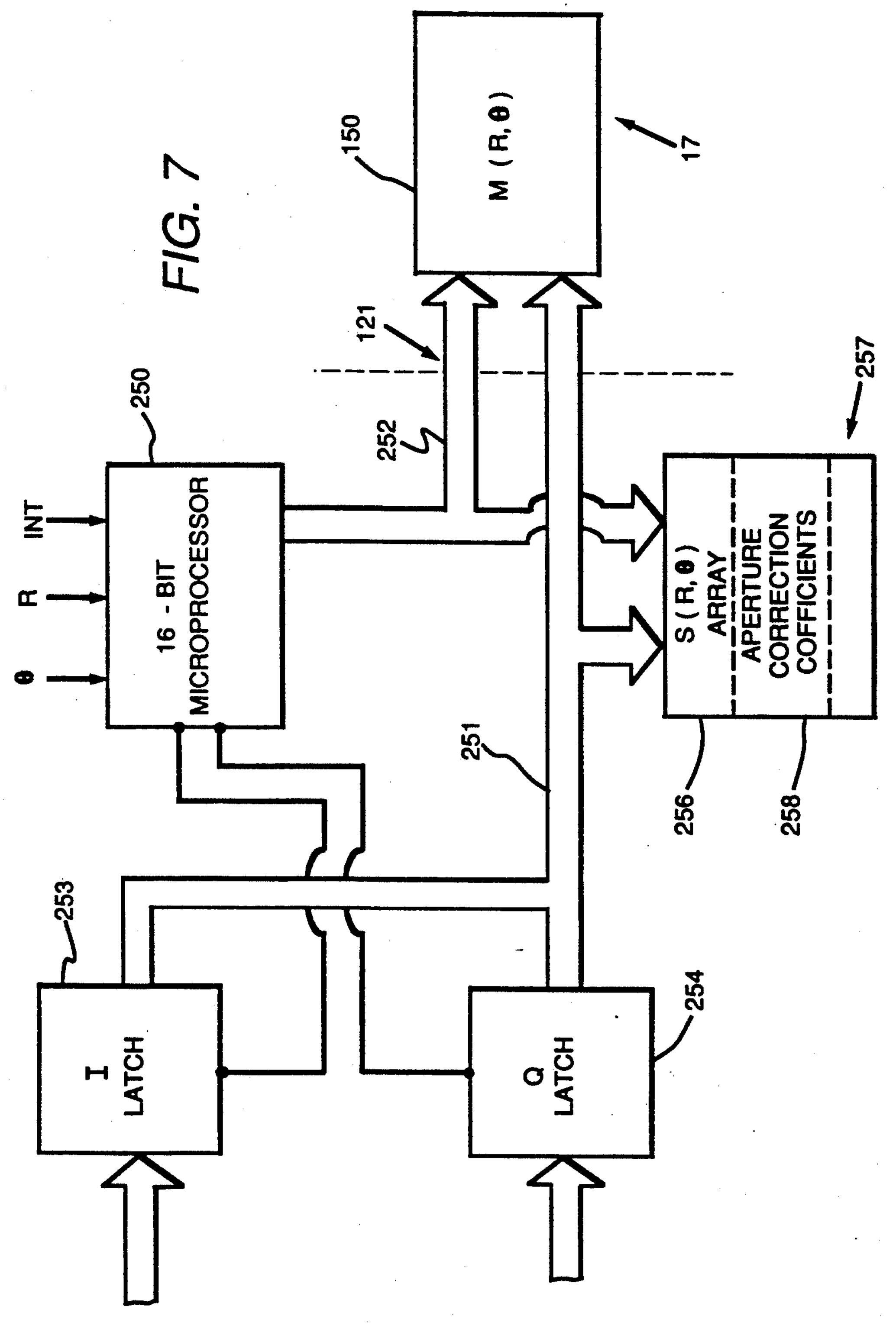
FIG. 7 is an electrical schematic diagram of the mid-processor which forms part of the receiver of FIG. 3.

Referring to FIG. 7, mid-processor 102 (FIG. 3) is formed around a 16-bit microprocessor 250 which drives a 16-bit data bus 251 and an address bus 252. Data bus 251 connects to a pair of input latches 253 and 254 which receive and store the respective I and Q components of the receive beam samples $S(R,\theta)$. When a new sample $S(R,\theta)$ is available in latches 253 and 254, microprocessor 250 is interrupted through a control line 255 from either latch and reads the I and Q values from the latches and stores them in the proper location in an $S(R,\theta)$ array 256 of a random access memory 257. Thus, as the system performs a scan under the direction of digital controller 16 (FIG. 1) to methodically produce receive beam sample data $S(R,\theta)$ at a succession of beam angles ($\theta$) and a succession of ranges (R) within each beam, microprocessor 250 is interrupted to store the sample data $S(R,\theta)$ in array 256. When a scan is complete, the process repeats and $S(R,\theta)$ array 256 is updated with new sample data.

Microprocessor 250 executes a stored program to methodically correct each beam sample $S(R,\theta)$ in array 256 using aperture correction coefficients 258 also stored in memory 257. The I and Q components of the corrected sample points $S'(R,\theta)$ are then combined as described above to form magnitude values $M(R,\theta)$ supplied to shared memory 150 in display system 17. A flow chart of that program is shown in FIG. 9.

Figure 8:
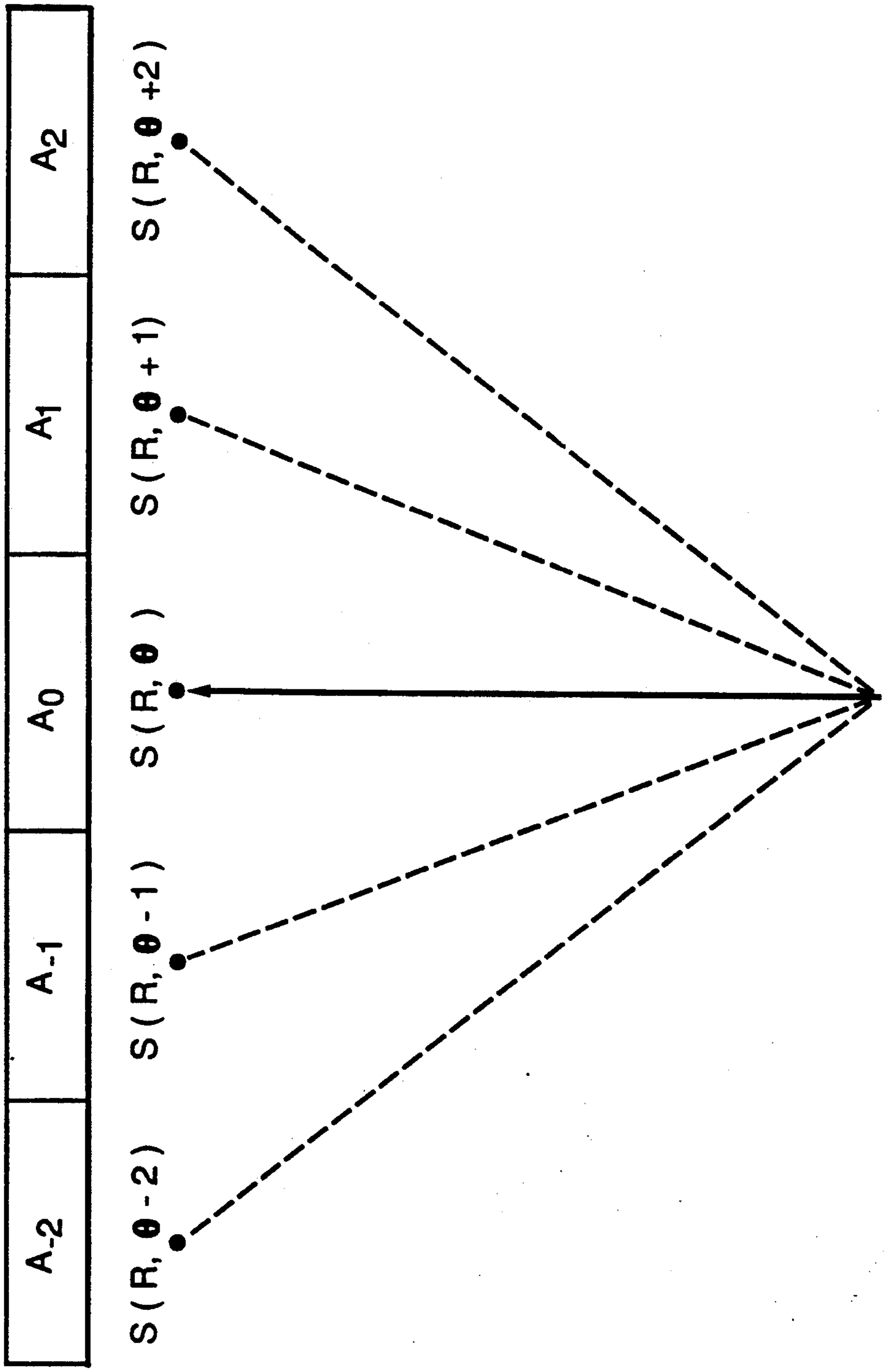
FIG. 8 is a pictorial view used to explain the correction process performed by the mid-processor of FIG. 7.
Figure 9:
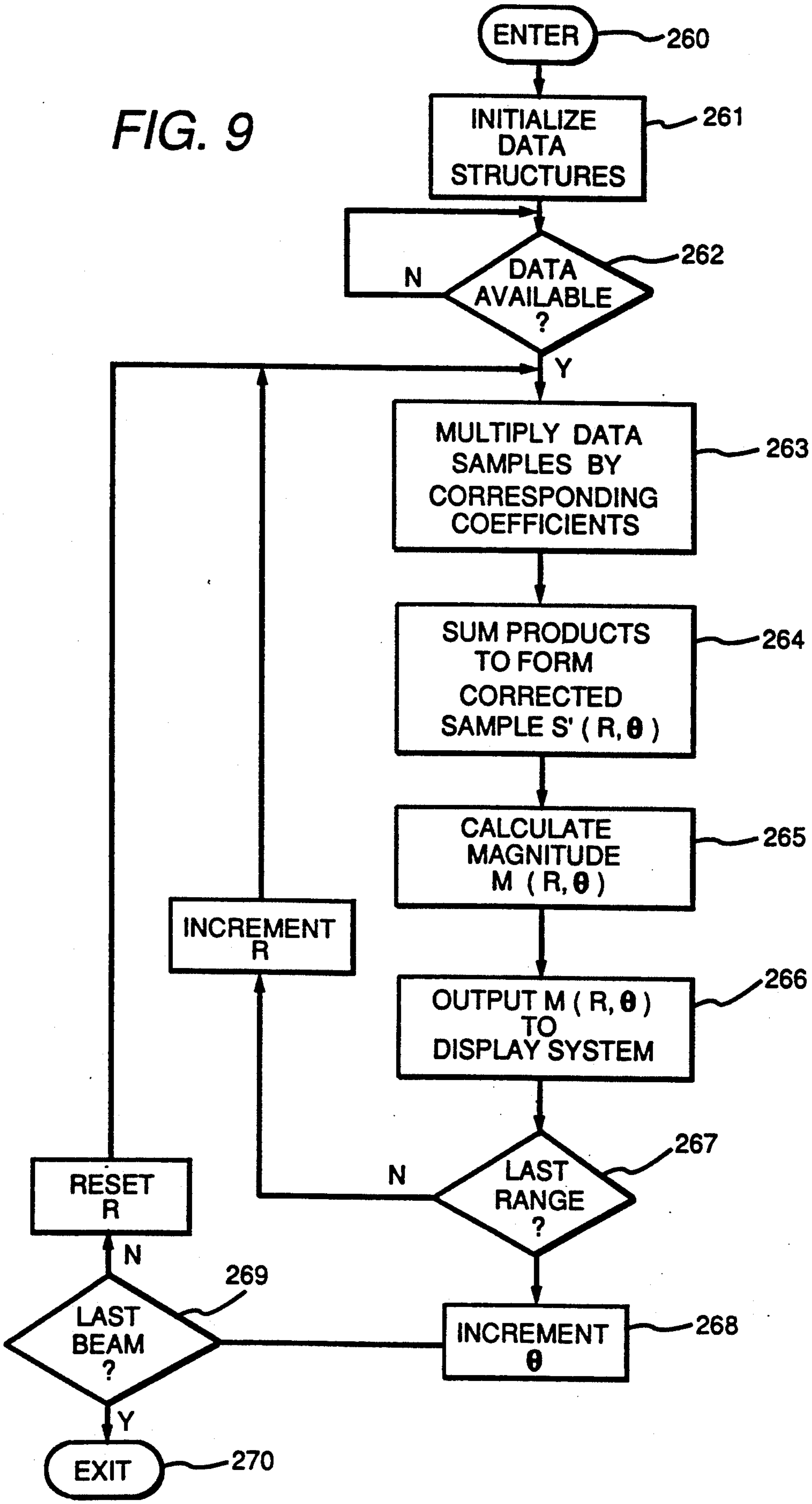
FIG. 9 is a flow chart of the correction program executed by the mid-processor of FIG. 7.

Referring to FIG. 9, the aperture correction program is entered at step 260 and data structures such as a range counter R and a beam counter $\theta$ are initialized at process step 261. The process then waits at decision point 262 until enough sample data $S(R,\theta)$ is available in array 256 (FIG. 7) to begin to make corrections. This occurs when the first three beams have been acquired, and corrections can be made on the first beam. A loop is then entered in which each successive beam sample $S(R,\theta)$ is corrected at process step 263. More specifically and as illustrated in FIG. 8, the complex data sample $S(R,\theta)$ and the two data samples disposed to each side of beam ($\theta$) at the same range R and in beams ($\theta-1$), ($\theta-2$), ($\theta$30 1) and ($\theta+2$) are each multiplied by a respective complex aperture correction coefficient $A_0$, $A_{-1}$, $A_{-2}$, $A_1$ and $A_2$. These coefficients are precalculated, as will be described below, and are stored in memory 257 (FIG. 7). In the preferred embodiment there are five aperture correction coefficients stored for each sampled location $(R,\theta)$. As indicated at process step 264, the five complex products are then summed to produce the corrected beam sample $S'(R,\theta)$, and the magnitude $M(R,\theta)$ of this complex number is calculated at process step 265 by calculating the square root of the sum of the squares of the I and Q components as described above. The corrected magnitude $M(R,\theta)$ is then supplied, at process block 266, to shared memory 150 in display system 17 (FIG. A).

The correction process continues for each sample on the receive beam ($\theta$) until the sample at the last range has been corrected, as determined at decision point 267. The beam counter $\theta$ is then incremented at step 268 to point at the next beam of sample data in S(R,$\theta$) array 256 (FIG. 7) and the system loops back to process the next receive beam. When the last beam in the scan has been processed, as determined at decision point 269, the program exits at step 270. The program may, of course, be reexecuted immediately to update display system 17 (FIG. 1) with new data on a real time basis.

The aperture correction coefficients 258 stored in mid-processor memory 257 (FIG. 7) are calculated off-line. A set of such coefficients must be calculated for each different transducer array geometry used with the system and for each different transmit focal distance ($R_0$) that is employed. Each such set is calculated by determining the corrections to be made to the receive beam sample data S(R,$\theta$) in order to implement the aperture function phase corrections as explained above:

$$\Delta\phi(k) = [2\pi/\lambda]\,(k - (N-1)/2)^2 d^2 \cos^2\theta \left[\frac{1}{2R} - \frac{1}{2R_0}\right]. \qquad (2)$$

The transmit aperture function may be expressed as:

$$T(k)=M(k)e^{j\Delta\phi(k)} \qquad (5)$$

where Δ100 (k) is the phase error at each transducer element due to the fixed transmit focus and M(k) is the ideal aperture function. The receive aperture function R(k) corresponds to the ideal aperture function M(k) because the system employs dynamic focusing during the receive mode. The total aperture function is the complex convolution of the transmit and receive aperture functions:

$$T/R(k)=T(k)*R(k)=M(k)e^{j\Delta\phi(k)}*M(k) \qquad ,(6)$$

where the operator (*) denotes convolution.

A discrete approximation of this total aperture function is as follows:

$$T/R(k) = \sum_{k'=0}^{N-1} T(k-k'))R(k') \qquad (7)$$

The desired, or corrected total aperture function is:

$$D(k)=M(k)*M(k)(k) \qquad (8)$$

and the corrections that must be made to the receive beam sample data S(R,$\theta$) are given by:

$$A(k)=D(k)/T/R(k) \qquad .(9)$$

The discrete Fourier transform of A(k) provides the filter coefficients A($\theta$) at all beam angles needed to make the corrections. Because of the impulse-like character of the filter coefficients, all coefficients need not be used. In the preferred embodiment only five filter coefficients and corresponding beam samples are employed and have been found to significantly improve image quality. In general, optimal filtering methods can be used to derive truncated sets of filter coefficients which match the desired beam forming characteristics in a least squares sense based on the basic inversion equation presented above.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A vibratory energy imaging system comprising:

a vibratory energy transducer array having a set of array elements disposed in a pattern and each being separately operable to produce a pulse of vibratory energy during a transmission mode and to produce an echo signal in response to vibratory energy which impinges thereon during a receive mode;

a transmitter coupled to the vibratory energy transducer array and being operable during the transmission mode to apply a separate signal pulse to each array element such that a steered transmit beam focused at a range $R_0$ is produced;

a receiver including a receive beam sample data array, said receiver being coupled to the vibratory energy transducer array and being operable during the receive mode to sample the echo signal produced by each array element as vibratory energy impinges thereon and to form a receive beam signal therefrom by summing the separate echo signals sampled from each array element to produce an array of receive beam sample data S(R,$\theta$), $\theta$ being the direction in which the transmit beam is steered, S identifying the sample, and R being the range to a vibrational energy reflecting object;

memory means for storing a set of aperture correction coefficients; and microprocessor means coupled to the memory means and the receive beam sample data array for producing corrected receive beam sample data S'(R,$\theta$) using the stored aperture correction coefficients to offset errors in the receive beam sample data S(R,$\theta$) which result from the range (R) being different than the focal range $R_0$ of the transmitter, S' identifying the corrected sample.

2. The vibratory energy imaging system recited in claim 1 wherein said memory means stores a number 2N+1 of aperture correction coefficients for each receive beam sample S(R,$\theta$), said receive beam sample data array stores sample data S(R,$\theta$) for a beam steered at angle $\theta$ and the N adjacent beams steered to each side of the angle $\theta$, and the corrected sample data S'(R,$\theta$) is produced by multiplying the respective 2N+1 aperture correction coefficients by the receive beam samples at S(R,$\theta$−N) through S(R,$\theta$+N) and summing the results of these multiplications.

3. The vibratory energy imaging system recited in claim 2 including a display system coupled to receive the corrected sample data S'(R,$\theta$) from the correcting means and to control brightness of a pixel in an image with each corrected sample data S'(R,$\theta$).

4. The vibratory energy imaging system recited in claim 3 wherein said transmitter scans a region by producing a series of transmit beams steered at a succession of closely spaced beam angles $\theta$, said receiver produces a corresponding series of receive beam signals and stores the receive beam sample data S(R,$\theta$) in said receive beam sample data array, and said microprocessor means successively corrects each beam sample data $S(R,\theta)$ therein so as to provide corresponding corrected sample data $S'(R,\theta)$ to the display system.

5. In a vibrational energy imaging system including a transducer array with separately operable array elements that each produce a pulse of vibrational energy during a transmission mode and produce an echo signal during a receive mode, a method of operation comprising:

a) applying a separate signal pulse, respectively, to each array element, respectively, during the transmission mode to produce a steered transmit beam focused at a range $R_O$;

b) forming a steered and dynamically focused receive beam signal during the receive mode by summing the separate echo signals produced by the array elements and producing an array of receive beam sample data $S(R,\theta)$, S identifying each sample, $\theta$ being the direction in which the transmit beam is steered and R being the range to a vibrational energy reflecting object;

c) correcting the receive beam sample data $S(R,\theta)$ for errors caused by the range (R) of the reflecting object being different than the focal range $R_0$ of the transmit beam; and d) producing an image with the corrected receive beam sample data.

6. The method recited in claim 5 including the step of storing a set of aperture correction coefficients for each sample data point $S(R,\theta)$ to be corrected.

7. The method recited in claim 6 including the steps of repeating steps a) and b) to acquire adjacent receive beam sample data points $S(R,\theta 30\ 1)$ and $S(R,\theta-1)$ and in which the step of correcting the receive beam sample data $S(R,\theta)$ in step c) comprises the operation of:

applying respective stored aperture correction coefficients for each sample data point $S(R,\theta)$ to the sample data point $S(R,\theta)$ and adjacent receive beam sample data points $S(R,\theta-1)$ and $S(R,\theta+1)$; and summing the results obtained in the operation of step c) to produce the corrected sample data $S'(R,\theta)$.

8. The method recited in claim 5 wherein step c) is performed by applying a set of stored aperture correction coefficients to the receive beam sample data $S(R,\theta)$.

* * * * *